(12) United States Patent
Castillo

(10) Patent No.: US 6,875,187 B2
(45) Date of Patent: Apr. 5, 2005

(54) OSTEO-ARTHRITIS KNEE BRACE

(75) Inventor: Edward L. Castillo, Laguna Hills, CA (US)

(73) Assignee: Innovation Sports, Inc., Foothill Ranch, CA (US)

( * ) Notice: Subject to any disclaimer, the term of this patent is extended or adjusted under 35 U.S.C. 154(b) by 497 days.

(21) Appl. No.: 10/163,046

(22) Filed: Jun. 5, 2002

(65) Prior Publication Data

US 2002/0183674 A1 Dec. 5, 2002

Related U.S. Application Data

(63) Continuation of application No. 09/484,006, filed on Jan. 18, 2000, now abandoned.

(51) Int. Cl.$^7$ ................................................. A61F 5/00
(52) U.S. Cl. ............................... 602/5; 602/16; 602/26
(58) Field of Search ............................... 602/5, 16, 23, 602/26; 128/882

(56) References Cited

U.S. PATENT DOCUMENTS

| | | | |
|---|---|---|---|
| 1,390,915 A | 9/1921 | Loth |
| 2,460,895 A | 2/1949 | Meany |
| 2,531,486 A | 11/1950 | Weber |
| 2,883,982 A | 4/1959 | Rainey |
| 3,030,634 A | 4/1962 | Blair |
| 3,099,448 A | 7/1963 | Salvo |
| 3,387,305 A | 6/1968 | Shafer |
| 3,669,105 A | 6/1972 | Castigia |
| 3,779,654 A | 12/1973 | Home |
| 3,785,372 A | 1/1974 | Craig |
| 3,817,244 A | 6/1974 | Taylor |
| 3,900,898 A | 8/1975 | Ackerman |
| 3,902,482 A | 9/1975 | Tayler |
| 3,928,872 A | 12/1975 | Ackerman |
| 3,958,569 A | 5/1976 | Johnson |
| 4,136,404 A | 1/1979 | Lange |
| 4,169,467 A | 10/1979 | Robischong et al. |
| 4,241,730 A | 12/1980 | Helfet |

(Continued)

FOREIGN PATENT DOCUMENTS

| | | |
|---|---|---|
| DE | 1491569 | 7/1969 |
| DE | 2432766 | 3/1975 |
| EP | 297766 | 4/1989 |
| WO | 8400533 | 11/1984 |

Primary Examiner—Michael A. Brown
(74) Attorney, Agent, or Firm—Stetina Brunda Garred & Brucker

(57) ABSTRACT

A knee brace including a lateral hinge component and a medial hinge component, a lower member encompassable about a lower leg portion and having a lateral element and a medical element each extending upwardly and connectingly engaged respectively to the hinge components, an upper member encompassable about an upper leg portion and having a lateral element extending downwardly and connectingly engaged to the lateral hinge component and a medial element extending downwardly to a distal end terminating above the medial hinge component. The distal end has a configuration non-obstructingly complementarity to an upper shape of the medial hinge component for full and uninterrupted flexion of the lower leg at the knee joint. A medially disposed arm is connectingly engaged to the medial hinge component and extends upwardly from the hinge component to be adjacent the medial element of the upper member for connection to each other with a releasably securable slidable engager. The arm and medial element are slidable and securable against each other to thereby laterally inwardly and outwardly position the upper member in angular relationship to the lower member and consequently treat inward or outward leg curvature through correction of knee joint orientation.

14 Claims, 2 Drawing Sheets

U.S. PATENT DOCUMENTS

| | | |
|---|---|---|
| 4,271,831 A | 6/1981 | Deibert |
| 4,361,142 A | 11/1982 | Lewis et al. |
| 4,372,298 A | 2/1983 | Lerman |
| 4,381,768 A | 5/1983 | Erichsen et al. |
| D269,379 S | 6/1983 | Bledsoe |
| 4,407,276 A | 10/1983 | Bledsoe |
| 4,428,369 A | 1/1984 | Peckham et al. |
| 4,487,200 A | 12/1984 | Feanny et al. |
| 4,489,718 A | 12/1984 | Martin |
| 4,493,316 A | 1/1985 | Reed et al. |
| 4,494,534 A | 1/1985 | Hutson |
| 4,503,846 A | 3/1985 | Martin |
| 4,523,585 A | 6/1985 | Lamb et al. |
| 4,554,913 A | 11/1985 | Womack et al. |
| D284,702 S | 7/1986 | Castillo |
| 4,599,998 A | 7/1986 | Castillo |
| 4,603,690 A | 8/1986 | Skeen |
| 4,614,181 A | 9/1986 | Karlsson |
| 4,620,532 A | 11/1986 | Houswerth |
| 4,621,624 A | 11/1986 | Rayboy |
| 4,628,916 A | 12/1986 | Lerman et al. |
| 4,665,905 A | 5/1987 | Brown |
| 4,681,097 A | 7/1987 | Pansier |
| 4,697,583 A | 10/1987 | Mason et al. |
| 4,699,129 A | 10/1987 | Aaserude et al. |
| 4,715,363 A | 12/1987 | Detty |
| 4,723,539 A | 2/1988 | Townsend |
| 4,753,240 A | 6/1988 | Sparks |
| D298,568 S | 11/1988 | Womack et al. |
| 4,791,916 A | 12/1988 | Paez |
| 4,803,975 A | 2/1989 | Meyers |
| 4,854,308 A | 8/1989 | Drillio |
| 4,856,501 A | 8/1989 | Castillo et al. |
| 4,886,054 A | 12/1989 | Castillo et al. |
| 4,938,207 A | 7/1990 | Vargo |
| 4,940,044 A | 7/1990 | Castillo |
| 4,955,369 A | 9/1990 | Bledsoe et al. |
| 4,964,402 A | 10/1990 | Grim et al. |
| 4,966,133 A | 10/1990 | Kausek |
| 4,986,264 A | 1/1991 | Miller |
| D318,736 S | 7/1991 | Castillo |
| 5,063,916 A | 11/1991 | France et al. |
| 5,086,760 A | 2/1992 | Neumann et al. |
| 5,121,742 A | 6/1992 | Engen |
| 5,135,469 A | 8/1992 | Castillo |
| 5,230,697 A | 7/1993 | Castillo et al. |
| 5,288,287 A | 2/1994 | Castillo et al. |
| D346,028 S | 4/1994 | Lengyel |
| 5,302,169 A | 4/1994 | Taylor |
| D357,070 S | 4/1995 | Castillo |
| 5,641,322 A | 6/1997 | Silver et al. |
| 5,669,873 A | 9/1997 | Towsley |
| 5,766,140 A | 6/1998 | Tillinghast, III et al. |
| D433,756 S | 11/2000 | Castillo |
| 6,309,368 B1 | 10/2001 | Herzberg |

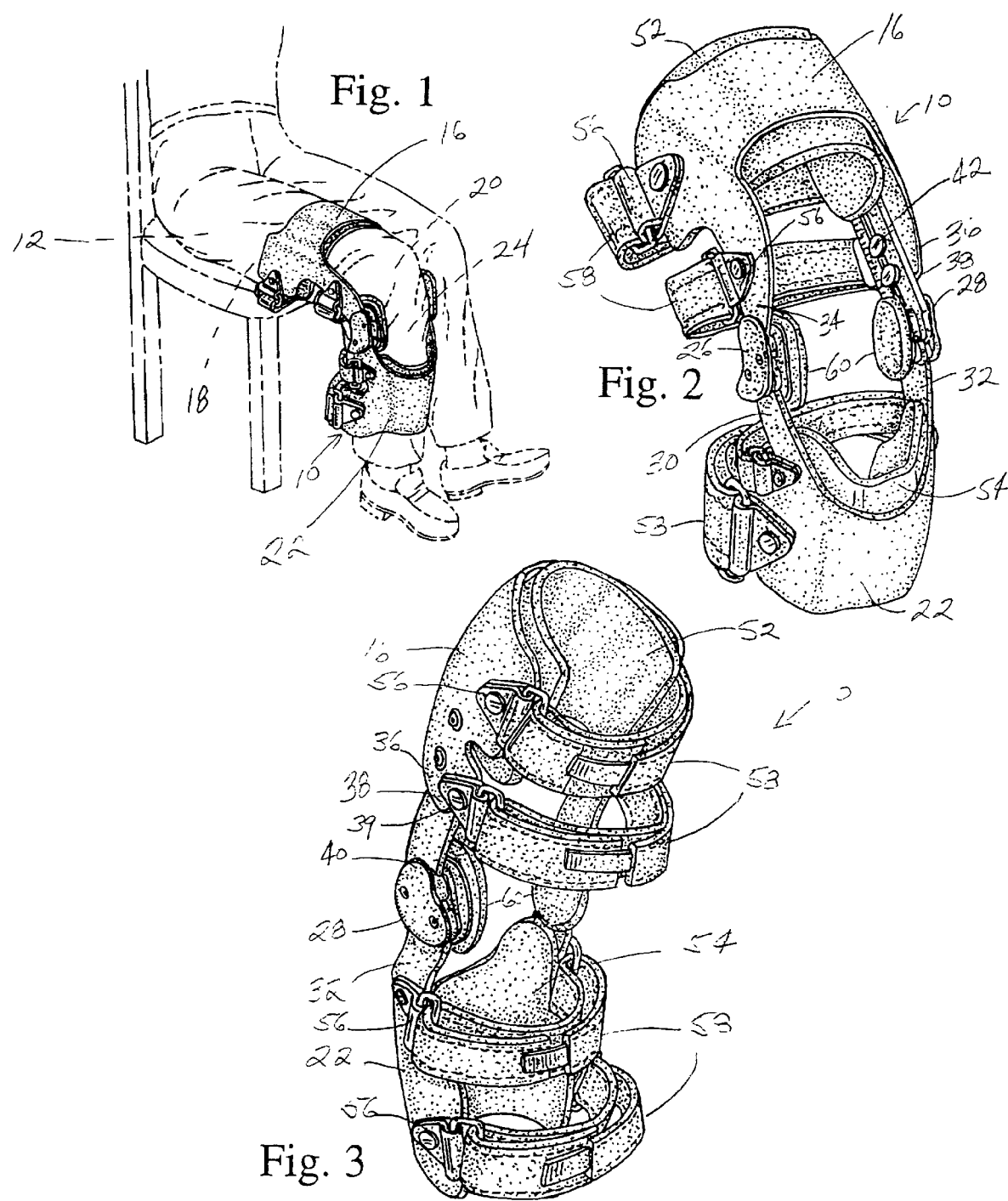

OSTEO-ARTHRITIS KNEE BRACE

This application is a continuation of U.S. Ser. No. 09/484,006, filed Jan. 18, 2000, now abandoned.

CROSS-REFERENCE TO RELATED APPLICATIONS (Not Applicable)

STATEMENT RE: FEDERALLY SPONSORED RESEARCH/DEVELOPMENT (Not Applicable)

FIELD OF THE INVENTION

The present invention relates in general to knee braces, and in particular to a knee brace for an osteo-arthritic knee joint wherein non-obstructed full flexion is attainable while laterally inward or outward joint disposition and resulting leg curvature are averted.

BACKGROUND OF THE INVENTION

Osteo-arthritis, also known as degenerative joint disease, is the most common form of arthritis and usually occurs after middle age. Especially vulnerable are knee joints where chronic breakdown of cartilage leads to pain, stiffness, and swelling. As the body tries to compensate for this infirmity, the knee joint may migrate laterally or outwardly, or it may migrate inwardly or medially, with the former condition often referred to as "bowlegged" and the latter referred to as "knock-kneed." When either event occurs, the leg experiences a corresponding curvature, the arthritic condition is not relieved, and the wearer continues to experience distress.

One manner of treating an osteo-arthritic knee condition is to fit the wearer with a knee brace whereby support is provided to allow reasonable ambulatory activity without undue risk of injury. In addition to providing ambulatory support, a prior art adjustable knee brace is available wherein releasably-securable angular adjustability of an upper brace portion above the knee joint of a wearer is laterally inwardly and outwardly movable with respect to a lower brace portion below the knee joint to thereby undertake straightening of the joint to overcome leg curvature. However, while this prior art brace with angularly-sideways adjustability addresses leg curvature, its functionality with respect to lower-leg flexion at the knee joint is impeded because certain interfacing hinge and brace members are not complimentarily configured for cooperating juxtaposed movement. Consequently, certain lateral-angle dispositions of the upper brace portion in relation to the lower portion cause an impact between the hinge and upper brace portion upon attempted full flexion by the wearer. This interference results in prohibiting full flexion and thereby can impede full mobility for the wearer.

In view of the above flexion constraint, it is apparent that a need is present for a knee brace capable of not only treating leg curvature, but also simultaneously permitting the wearer to achieve full leg flexion at the knee joint. Accordingly, a primary object of the present invention is to provide a knee brace for the treatment of osteo-arthritis wherein treatment of leg curvature is addressed while concurrent complete flexion at the knee joint of a wearer is permitted.

Another object of the present invention is to provide a knee brace wherein interfacing hinge and brace members are complimentarily configured for cooperating juxtaposed movement during leg flexion over all relative lateral-angle placement positions between upper and lower brace portions.

These and other objects of the present invention will become apparent throughout the description thereof which now follows.

SUMMARY OF THE INVENTION

The present invention is a knee brace for supporting a leg of a wearer whose knee joint is affected by osteo-arthritis. The brace first includes a lateral hinge component and a medial hinge component positionable respectively laterally and medially adjacent the knee joint of the wearer. Second, the brace embodies a lower member at least partially surroundingly encompassable about a lower leg portion situated below the knee joint of the wearer. This lower member has a lateral element and a medial element each extending upwardly and connectingly engaged respectively to the lateral hinge component and medial hinge component for extension-flexion movement. Third, the brace incorporates an upper member at least partially surroundingly encompassable about an upper leg portion situated above the knee joint of the wearer. The upper member has a lateral element extending downwardly and connectingly engaged to the lateral hinge component for extension-flexion and horizontal pivotal movements, and a medial element extending downwardly to a distal end terminating above the medial hinge component. This distal end is terminally, complimentarily, non-obstructingly configured to an upper shape of the medial hinge component to thereby permit full and uninterrupted flexion of the lower leg at the knee joint. A medially disposed arm is connectingly engaged to the medial hinge component and is movable for both extension-flexion and horizontal pivotal movements. The arm extends upwardly from the medial hinge component to be adjacent the medial element of the upper member, and the arm and medial element are connected to each other with a releasably securable slidable engager. In this manner the arm and medial element are selectively vertically slidable and securable against each other to thereby laterally inwardly and outwardly selectively and retainably position the upper member in angular relationship to the lower member.

As is apparent, correction of leg curvature is accomplished by selecting and securing an appropriate lateral inward or outward angle of the upper member in relation to the lower member. For example, if the wearer suffers from an outward or bowlegged curvature, the upper member is angled laterally outwardly to thereby force the knee joint medially. Conversely, if the wearer has an inward or knock-kneed curvature, the upper member is angled inwardly to thereby force the knee joint laterally. Meanwhile, because the distal end of the medial element extending downwardly from the upper member is terminally, complimentarily, and non-obstructingly configured to the upper shape of the medially disposed hinge component as recited above, the wearer experiences full and uninterrupted flexion of the lower leg at the knee joint irrespective of the magnitude or direction of the lateral inward or outward angular slant of the upper member in relation to the lower member. When the brace is fitted with length-adjustable straps for securement thereof to the leg, only a minimal size selection (e.g. small, medium, large) need be produced since fit-range flexibility is achieved through the adjustable straps. As is therefore apparent, the present knee brace provides full-flexion capability coupled with inward-outward selectable angularity of the upper member thereof to readily treat osteo-arthritis by maintaining a non-curvature leg profile.

BRIEF DESCRIPTION OF THE DRAWINGS

An illustrative and presently preferred embodiment of the invention is shown in the accompanying drawings in which:

FIG. 1 is a perspective view of a knee brace in place on a wearer, said wearer and a chair therefor shown in phantom;

FIG. 2 is a front perspective view of the knee brace of FIG. 1;

FIG. 3 is a rear perspective view of the knee brace of FIG. 1;

DETAILED DESCRIPTION OF THE PREFERRED EMBODIMENT

Figure 4:
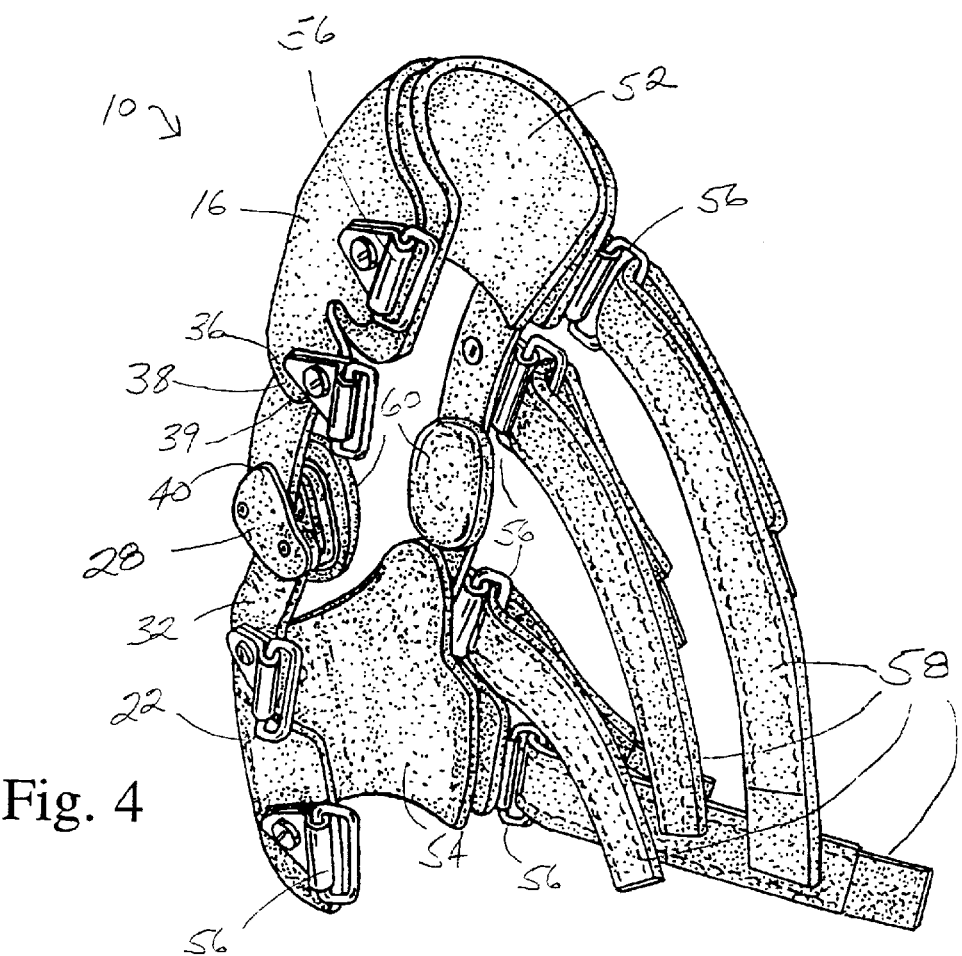
FIG. 4 is a rear perspective view of the knee brace of FIG. 1 with attachment straps disengaged.

Referring to FIGS. 1–4, a knee brace 10 for supporting a leg 12 of a wearer is illustrated. The brace 10 has an upper member 16 partially surroundingly encompassable about an upper leg portion 18 situated above the knee joint 20 of the wearer, and a lower member 22 partially surroundingly encompassable about a lower leg portion 24 situated below the knee joint 20 of the wearer. A lateral hinge component 26 and a medial hinge component 28 are positionable respectively laterally and medially adjacent the knee joint 20. The lower member 22 has a lateral element 30 and a medial element 32 each extending upwardly and respectively engaged to the lateral hinge component 26 and medial hinge component 28 for extension-flexion movement. The hinge components 26, 28 are ratio swing hinges constructed according to the disclosure in U.S. Pat. No. 4,940,044, incorporated herein in its entirety by reference. These hinge members 26, 28 are thus specifically designed to closely simulate rotational movement of the tibia relative the femur, whereby the pivot point of the hinge varies or changes during rotational movement of the tibia relative the femur, to thereby closely simulate normal knee movement. All connections herein to the hinge components 26, 28 are as described in the referenced patent.

Figure 5:
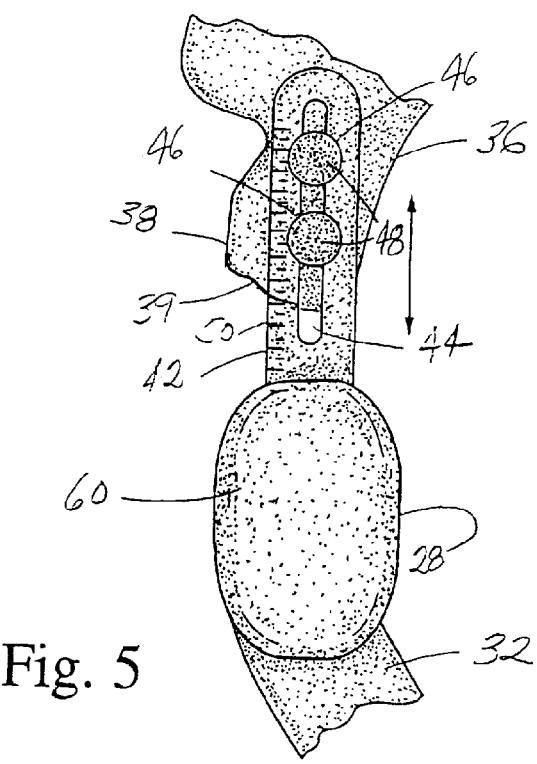
FIG. 5 is an elevation view of a releasably securable slidable engager for angularly positioning upper and lower brace members in relation to each other.

The upper member 16 has a lateral element 34 extending downwardly and engaged to the lateral hinge component 26 for extension-flexion movement and such that minimal horizontal pivotal movement at the point of engagement to the lateral hinge component 26 can occur because of play at such point. Also extending downwardly from the upper member 16 is a medial element 36 having a distal end 38 terminating above the medial hinge component 28 and having a configuration 39 non-obstructingly complimentarily with an upper shape 40 of the medial hinge component 28. A medially disposed arm 42 with a slot 44 (FIGS. 2 and 5) is connectingly engaged to the medial hinge component 28 for extension-flexion movement and horizontal pivotal movement at the point of engagement to the medial hinge component 28 in the same manner as earlier described in relation to connection of the lateral element 34 to the lateral hinge component 26. The arm 42 extends upwardly to be disposed adjacent the medial element 36 of the upper member 16, with the arm 42 and medial element 36 connected to each other with a releasably securable slidable engager here being two conventional threaded cylindrical fasteners 46 passing through the slot 44 and each having a base disc 48 at one end and a tightenable screw (not shown) on the other. In this manner, the arm 42 and medial element 36 are selectively vertically slidable and securable against each other for laterally inwardly and outwardly selectively and retainably positioning the upper member 16 in angular relationship to the lower member 22. A marked gradient 50 is provided on the arm 42 adjacent the slot 44 such that a desired placement can be duplicated at a later time.

Both the upper member 16 and lower member 22 are preferably constructed of a thermoplastic resin fitted on the inner surfaces thereof with respective conventional pads 52, 54 for comfort, and provided with attached conventional loop hardware 56 for accommodating lengths of conventionally constructed hook-and-loop straps 58 respectively threadable through the loop hardware 56 and thereby length-adjustable to be tightened about the upper and lower leg portions 18, 24. The inner surfaces of the respective hinge components 26, 28 likewise are provided with pads 60 for wearer comfort.

In use, a physician or other care specialist positions the upper and lower members 16, 22 relative each other laterally such that, when viewing the knee brace 10 from the rear, the lower member is vertical (referenced as 0°) and the upper member 16 is slanted to the left or to the right over an arc between about −15° (left slant) to about +15° (right slant). Such angular positioning is previously determined by conventionally measuring the magnitude of inward or outward leg curvature exhibited by the wearer, and may need to be gradually increased over time as the wearer responds to such leg straightening therapy. When desired angular placement of the upper member 16 is reached, the fasteners 46 are threadably tightened and the brace 10 is ready for fitting. In particular, a wearer places the upper member 16 around the upper leg portion 18 and the lower member 22 around the lower leg portion 24 such that the hinge components 26, 28 are adjacent the sides of the knee joint 20. The straps 58 then are tightened adequately to firmly secure the brace 10 to the leg 12 and thereby provide re-orientation of the knee joint 20 medially or laterally as indicated to maintain treatment of osteo-arthritic cartilage breakdown.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A knee brace for supporting a leg of a wearer whose knee joint is affected by osteo-arthritis, the brace comprising:

a) a lateral hinge component and a medial hinge component positionable respectively laterally and medially adjacent the knee joint, the lateral hinge component and the medial hinge component each being formed as a ratio swing hinge;

b) a lower member at least partially circumscribable about a lower leg portion situated below the knee joint of the wearer, said lower member having a lateral element and a medial element each extending upwardly and connectingly engaged respectively to the lateral hinge component and medial hinge component for extension-flexion movement;

c) an upper member at least partially circumscribable about an upper leg portion situated above the knee joint of the wearer, said upper member having a lateral element extending downwardly and connectingly engaged to the lateral hinge component providing play at a point of engagement between said lateral element and said lateral hinge component for extension-flexion and horizontal pivotal movements, and a medial element extending downwardly to a distal end terminating above the medial hinge component, said distal end having a configuration non-obstructingly to an upper shape of said medial hinge component; and d) a medially disposed arm connectingly engaged to the medial hinge component for extension-flexion and horizontal pivotal movement and extending upwardly therefrom adjacent the medial element of the upper member, with said arm and said medial element connected to each other with a releasably securable slidable engager whereby said arm and medial element are selectively vertically slidable and securable against each other along a slot formed adjacent a marked gradient on said arm for laterally inwardly and outwardly selectively and retainably positioning the upper member in angular relationship to the lower member.

2. A knee brace as claimed in claim 1 wherein the slidable engager is at least one threaded cylindrical fastener passing from the medial element through said slot, and at least one threaded tightener engaged with the at least one cylindrical fastener and threadably movable thereon such that the medial element and arm are releasably securable against each other.

3. A knee brace as claimed in claim 1 wherein the upper member is laterally inwardly and outwardly selectively angularly and retainably positionable in relation to the lower member over an arc between about −15° and +15° as measured from a non-angular position of 0°.

4. A knee brace an claimed in claim 3 wherein angular retainment is between about −1° and −15° for maintaining the knee joint and leg in a non-inwardly curved position.

5. A knee brace as claimed in claim 3 wherein angular retainment is between about +1° and +15° for maintaining the knee joint and leg in a non-outwardly curved position.

6. A knee brace as claimed in claim 1 wherein the upper member and lower member are sized and configured to circumscribe respective forward halves of the upper and lower leg portions and wherein length-adjustable straps respectively extend from said upper and lower members for releasably circumscribing respective rear halves of said leg portions.

7. A knee brace as claimed in claim 6 wherein each of said length-adjustable straps has hook and loop fasteners for releasably maintaining a length of said strap.

8. A knee brave for supporting a leg of a wearer whose knee joint is affected by osteo-arthritis, the brace comprising:
   a) a lateral hinge component and a medial hinge component positionable respectively laterally and medially adjacent the knee joint;
   b) a lower member at least partially circumscribable about a lower leg portion situated below the knee joint of the wearer, said lower member having a lateral element and a medial element each engaged respectively to the lateral hinge component and medial hinge component for extension-flexion movement;
   c) an upper member at least partially circumscribable about an upper leg portion situated above the knee joint of the wearer, said upper member having a lateral element engaged to the lateral hinge component for extension-flexion and horizontal pivotal movements, and a medial element terminating above the medial hinge component; and
   d) a medially disposed arm engaged to the medial hinge component for extension-flexion and horizontal pivotal movement and extending upwardly therefrom to be connected to said medial element with a slidable engager whereby said arm and medial element are selectively vertically slidable and securable against each other along a slot formed adjacent a marked gradient on said arm for laterally inwardly and outwardly selectively and retainably positioning the upper member in angular relationship to the lower member.

9. A knee brace as claimed in claim 8 wherein the slidable engager is at least one threaded cylindrical fastener passing from the medial element through said slot, and at least one threaded tightener engaged with the at least one cylindrical fastener and threadably movable thereon such that the medial element and arm are releasably securable against each other.

10. A knee brace as claimed in claim 8 wherein the upper member is laterally inwardly and outwardly selectively angularly and retainably positionable in relation to the lower member over an arc between about −15° and +15° as measured from a non-angular position of 0°.

11. A knee brace as claimed in claim 10 wherein angular retainment is between about −1° and −15° for maintaining the knee joint and leg in a non-inwardly curved position.

12. A knee brace as claimed in claim 10 wherein angular retainment is between about +1° and +15° for maintaining the knee joins and leg in a non-outwardly curved position.

13. A knee brace as claimed in claim 8 wherein the upper member and lower member are sized and configured to circumscribe respective forward halves of the upper and lower leg portions and wherein length-adjustable straps respectively extend from said upper and lower members for releasably circumscribing respective rear halves of said leg portions.

14. A knee brace as claimed in claim 13 wherein each of said length-adjustable straps has hook and loop fasteners for releasably maintaining a length of said strap.

* * * * *